United States Patent [19]

Watanabe et al.

[11] 4,101,523

[45] Jul. 18, 1978

[54] POLYESTER FILMS

[75] Inventors: Masamichi Watanabe, Yokohama; Takuo Nakahara; Seiji Sakamoto, both of Machida; Kunio Bizen, Yokohama; Akikazu Yano, Yokohama; Yuzo Otani, Yokohama, all of Japan

[73] Assignee: Mitsubishi Chemical Industries Limited, Tokyo, Japan

[21] Appl. No.: 705,936

[22] Filed: Jul. 16, 1976

[30] Foreign Application Priority Data

Jul. 17, 1975 [JP] Japan .................................. 50/87480
Jul. 18, 1975 [JP] Japan .................................. 50/87937
Jul. 18, 1975 [JP] Japan .................................. 50/87935

[51] Int. Cl.² ............................................. C08G 63/22
[52] U.S. Cl. .................................. 528/309; 528/275; 528/305; 526/4
[58] Field of Search .......................... 260/75 T, 75 M

[56] References Cited

U.S. PATENT DOCUMENTS

| 3,567,693 | 3/1971 | Piirma .............................. 260/75 M |
| 3,657,180 | 4/1972 | Cohn .............................. 260/75 M X |

FOREIGN PATENT DOCUMENTS

| 49-21100 | 5/1974 | Japan. |
| 42-24099 | 11/1967 | Japan. |

*Primary Examiner*—Walter C. Danison
*Attorney, Agent, or Firm*—Lane, Aitken, Dunner & Ziems

[57] ABSTRACT

A polyester film is disclosed which comprises a polyester mainly consisting of polyethylene terephthalate and an additive amount of granular calcium terephthalate anhydride particles having a specific volume shape factor. The average particle diameter and additive amount of the granular calcium terephthalate anhydride particles may be controlled so that the film is particularly suitable as a metallized film or a condenser film.

2 Claims, 6 Drawing Figures

POLYESTER FILMS

FIELD OF THE INVENTION

This invention relates to a polyester film which includes granular calcium terephthalate anhydride particles having a volume shape factor within a certain range.

BACKGROUND OF THE INVENTION

Polyesters mainly consisting of polyethylene terephthalate having a high degree of crystallinity and a high softening point are widely used in various commercial fields, because they have excellent properties such as stretchability, flexural strength, chemical resistance, light resistance, heat resistance and the like. A polyester may be formed into a film depending upon the intended service of the products. However, it is known that such a film has deficiencies in that the film is easily electrostatically charged and abraded by guide members and hand slipperiness is insufficient. It is also known that these troubles can be eliminated by improving the slipperiness of the polyester film. Proposals have been made to employ antistatic agents or lubricants to improve the slipperiness. However, these methods cannot be easily utilized because of reduced electrical properties, low operation efficiency, and increased cost.

While various methods for improving the slipperiness have been proposed, the most usual is to distribute fine particles of an inert material at the surface of a film. In general, fine particles can be incorporated by the following two methods.

In the first, a precipitation method, a calcium compound catalyst which is used in an ester-interchange reaction is precipitated during the polycondensation reaction in the form of fine particles of calcium terephthalate and a calcium salt of polyester oligomer (both of which are insoluble in the polyester). Terephthalic acid may be added to the reaction system to facilitate the precipitation of fine particles. In still another method, terephthalic acid and calcium acetate may be added at the stage of polycondensation to precipitate calcium terephthalate particles. In all of these cases, fine particles are precipitated from within the reaction system.

A second method is called the addition method. Silica, kaolin, talc or the like, after pulverization if necessary, is added either to a polyester-forming reaction system or to a polyester compound before molding.

Calcium terephthalate as such can be formed in a polyester according to the above-described precipitation method. The calcium terephthalate particles precipitated the polyester may be used to improve the slipperiness. It is, however, difficult to control the degree of slipperiness. In addition, the calcium terephthalate precipitated in the polyester are inclined to be broken during stretching in the course of film formation and consequently a slipperiness of the formed film will be far below the level expected from a calcium terephthalate containing polyester before the film formation.

The film is required to have abrasion resistance as well as slipperiness. Particularly when the film is used as a magnetic tape, the abrasion of the film by magnetic heads and other guide members should be small. Less satisfactory properties result from the prior art precipitation method making use of fine particles of calcium terephthalate precipitated in the polyester.

SUMMARY OF THE INVENTION

It is an object of this invention to provide a polyester film in which the slipperiness and abrasion resistance are improved without substantially impairing the clearness.

The above and other related objects and features of the invention will be made apparent in the following description of the disclosure.

The inventors have made extensive investigations to develop a polyester film which has an improved slipperiness and abrasion resistance as well as an acceptable clearness; and have found that a film improved in various properties can be obtained by blending a specified amount of granular calcium terephthalate particles which are prepared separately outside the reaction system and have a specific particle shape and size.

According to the present invention, there is provided a polyester film comprising a polyester mainly consisting of polyethylene terephthalate and including granular calcium terephthalate anhydride particles which have a volume shape factor $\phi_v$ represented by the following formula:

$$\phi_v = V/D^3$$

wherein D is the maximum diameter of a particle in the projection plane (micron) and V is the volume of the particle (cubic microns), of 0.08 to 0.4.

BRIEF EXPLANATION OF THE DRAWINGS

FIGS. 1-a, 1-b and 1-c show models of particles which are used for calculating the volume shape factor $\phi_v$ and FIGS. 2-a, 2-b and 2-c show microscopic photographs of granular particles (a,b) of calcium terephthalate anhydride and needle particles (c) of non-dewatered calcium terephthalate, respectively.

DETAILED DESCRIPTION OF THE INVENTION

The polyester used herein is formed from terephthalic acid or its lower alkyl ester and ethylene oxide or ethylene glycol, and if desired, at least one additional component. The polyester of the invention may include flame retardants, anti-coloring agents, antistatic agents, heat resistant agents, light resistant agents and other modifiers, without departing from the spirit and scope of the invention.

The granular calcium terephthalate to be added to the polyester should be its anhydride, which may be prepared in any desired manner. A most simple method is described below.

A dialkali metal terephthalate, such as a potassium salt or sodium salt is reacted with a water-soluble calcium compound, such as calcium chloride or calcium nitrate in water to give calcium terephthalate which is in the form of plate-like crystals. The plate calcium terephthalate is ground and classified before or after it is heated at a temperature of more than 100° C, preferably from 150° to 200° C, to convert it into the anhydride. In the milling step, for example, a jet mill, fluid energy mill or ball mill may be used to grind the calcium terephthalate (or its anhydride). Any of these milling means can easily mill almost all of the plate crystals of calcium terephthalate into granular particles.

The resulting ground particles are then classified to obtain a portion of particles which have a particle size within a certain range suitable to add to the polyester. In the classification step, for example, a semi-free vortex classifier, forced vortex classifier, hydrocyclone or centrifugal separator may be used.

The granular particles which can be employed in the invention should have a volume shape factor $\phi_v$ of 0.08 to 0.4. The volume shape factor is represented by the following formula:

$$\phi_v = V/D^3$$

In the formula, D is the maximum diameter of a particle in the projection plane (micron) and V is the volume of the particle (cubic microns). It is to be noted that the factor $\phi_v$ for all the particles in a group is an arithmetic mean of these for individual particles. The factor $\phi_v$ represents the degree of particle size. The shape of a particle will be exactly granular or spherical when the value of the factor $\phi_v$ approaches $\pi/6$.

The calcium terephthalate employed herein should be an anhydride as described above. Sticking water and water of crystallization should be removed before calcium terephthalate particles are added to a polyester-forming system, because particles having water of crystallization readily change into needle particles in the presence of ethylene glycol. Furthermore, if calcium terephthalate having water of crystallization is added to a polyester, the latter may be undesirably colored. For example, sodium terephthalate is reacted with calcium chloride in an aqueous medium to precipitate calcium terephthalate. The precipitate is then dried at a comparatively low temperature below 100° C to remove sticking water only or sticking water and part of water of crystallization. If such partly dried calcium terephthalate particles are added during the polyethylene terephthalate reaction process, the resulting polyethylene terephthalate is inevitably colored. This is also true for the calcium terephthalate particles which are produced from the calcium terephthalate forming reaction in ethylene glycol as a medium. Namely, the calcium terephthalate particles produced from afore said reaction should be heated at a temperature above the boiling point of ethylene glycol to remove the sticking ethylene glycol and ethylene glycol of crystallization, before being added to a polyester-forming system.

The calcium terephthalate particles used herein is added to a polyester-forming reaction system or to a molten polyester before molding. A slurry of fine particles in ethylene glycol may preferably be added to prevent fine particles from dissipating, to automatically weight the quantity of particles, and to facilitate the dispersion of particles in a polymer. In practice, a slurry containing 5 – 20% by weigh of calcium terephthalate is particularly suitable.

Instead of the ethylene glycol slurry, a master batch of a polymer containing calcium terephthalate in high concentrations may preferably be added to a polymerization system or to a molten polyester before molding.

As described above, to a polyester-forming reaction system in which a polyester-insoluble compound precipitated from within the system is present or absent, calcium terephthalate particles which are separately prepared outside the reaction system are added according to the invention. The resulting polyester compound is molten and extruded into a film, which is then stretched by 2.5 to 4.5 times in both the longitudinal and the crosswise directions and if desired, subjected to thermal fixation.

The resulting film shows satisfactory slipperiness and abrasion resistance as well as adequate clearness. Inter alia, a polyester film which includes a specified amount of calcium terephthalate anhydride particles having a particle size within a certain range is particularly suitable as a metallizing film or a condenser film, depending upon the particle size and additive amount of particles.

The metallizing polyethylene terephthalate film is a film on which any metal such as aluminum can be deposited to form a metallized film having improved properties for the application to metallic strings and stamping foils.

A metallic string made of a polyethylene terephthalate film is generally prepared by vacuum depositing a metal, for example, aluminum or silver on the surface of a biaxially stretched polyethylene terephthalate film. The metallized film is then coated with an epoxy or polyurethane resin to obtain the metallized film covered with a white coating, which is then cut into strips, which are in turn woven into a string by means of a weaving machine. On the other hand, a stamping foil is prepared by applying a surface lubricant on the surface of a biaxially stretched polyethylene terephthalate film, vacuum depositing a metal, and then applying an adhesive. There is obtained a laminate consisting of the film, lubricant, metal, and adhesive layers. On use, the laminate is superposed on any desired object to be stamped, with the adhesive layer in contact with the object. Then a heated stamp is pressed to the laminate at the film side so that the portions of the metallized layer on which protrusions of the stamp abut are transferred to the object. The golden or silvery pattern which corresponds to an image on the stamp is duplicated.

Polyester films, inter alia, polyethylene terephthalate films are widely used in various fields due to their improved clearness, mechanical properties, chemical resistance and the like, despite their low slipperiness. The lack of slipperiness is a serious problem resulting in reduced operation efficiency when the polyethylene terephthalate films are wound up. Lubricants are usually added to a film composition in order to increase the slipperiness. However, a commercially available lubricant, for example, a metallic soap, natural wax, higher fatty acid, etc. may decompose at the extrusion temperature of polyethylene terephthalate so that the addition of such a lubricant may fail to attain the desired effect. Another proposal to increase the slipperiness is to add inert fine particles to roughen the surface of a film. In general, the addition of inert fine particles may result in loss of clearness and hence an opaque film which is unsuitable for the production of metallic strings. It is therefore eagerly desired to develop an additive which can minimize the loss in film clearness and a method of adding the same.

The inventors have found that when a metallized film is to be wound, numerous scratches are often formed in the metallic layer in the mechanically stressed direction due to the contact between the metallic surface and the film surface. (Microscopic examination reveals that the metal is partly stripped off at scratches.) As a result, a final product is considerably damaged.

To obviate the above drawbacks, the inventors have made experiments on various additives and found that calcium terephthalate anhydride is most preferred as an additive. More precisely, the inventors have found that the addition of calcium terephthalate anhydride in a specified amount to polyethylene terephthalate ensures to obtain a laminate by depositing a metal coating on a polyethylene terephthalate film, which laminate shows substantially no difference in luster between the metallic side and the film side, is formed with minimum scratches in the metallic surface upon winding, and is easy to handle.

In one embodiment of the invention, there is provided a metallized film which comprises a polyester mainly consisting of polyethylene terephthalate including 0.02 to 0.3% by weight of calcium terephthalate anhydride having a volume shape factor $\phi_v$ of 0.08 to 0.4 and an average particle diameter of 0.2 to 3.0 microns. The product of the average particle diameter (micron) and the additive amount (wt%) should be 0.03 to 0.15.

Upon the addition of calcium terephthalate particles, it is essential that the particle size and the additive amount meet the specified requirements according to the invention. The particle size is defined in terms of the operation efficiency, difference between the right side and the reverse side, and appearance of the final film. According to the invention, the average particle diameter which is determined by the method described hereinafter should be from 0.2 to 3.0 microns, preferably from 0.2 to 2.0 microns. If particles have an average particle diameter of below 0.2 micron, the operation efficiencies including the friction coefficient are insufficient. On the other hand, if the diameter exceeds 3 microns, not only the difference between the right side and the reverse side of a film is adversely affected, but also the surface of the film is rough to the naked eye and therefore, its appearance is poor. The amount of calcium terephthalate anhydride to be added should be 0.02 to 0.3%, preferably 0.05 to 0.2% by weight from the standpoint of clearness, operation efficiency, filter life, and the like. If the amount is less than 0.02% by weight, wrinkles are inevitably generated during slitting. On the other hand, if the amount exceeds 0.3% by weight, other problems are encountered with respect to the filter life (the life of a filter placed in an extruder) lower production efficiency is, and scratches may readily form when processed into a metallized film.

Furthermore, the product of the average particle diameter (micron) and the additive amount (wt%) should be within the range from 0.03 to 0.15 so as to meet the requirements concerning the difference between the right side and the reverse side of a film, scratch resistance of a metallized layer, and friction coefficient. If the product contains less than 0.03, the friction coefficient becomes too large. If the product contains more than 0.15, the difference between the right side and the reverse side is distinguishable and scratches may be easily formed. The measure which determines whether scratches are easily formed or not is given by $T_1$ and $T_2$ which are evaluated by the method of determining scratches as described hereinafter. $T_1$ and $T_2$ may preferably be less than 2.0% and 2.5%, respectively. If $T_1$ and $T_2$ are above these values, respectively, scratches on the metallic surface are apparent to the naked eye and consequently the final product is of low quality.

The polyethylene terephthalate film of the invention is very suitable as a metallized film to be used for metallic strings and stamping foils, because it is highly improved in requisite properties such as the friction coefficient (the static friction coefficient of a film should be less than 2.5 and the dynamic friction coefficient should be less than 2.0 in order to ensure the operation efficiency sufficiently high), difference between the right side and the reverse side, and scratch resistance ($T_1 <$ 2.0 and $T_2 < 2.5$).

The polyester film including the specified amount of calcium terephthalate anhydride having a particle size within the given range is also suitable for use as a condenser film.

It has become desirable in recent years to miniaturize condensers. To this end, a biaxially stretched polyethylene terephthalate film tends to replace conventional impregnated paper because polyethylene terephthalate can be formed into a thin and uniform film which has an improved dielectric breakdown voltage over the impregnated paper. A comparatively sophisticated film-forming technique is required to form polyethylene terephthalate into a thin film. With the advance in the film-forming method, it is now possible to manufacture a super thin film as thin as 2.5 microns.

However, thin films have encountered serious problems. The thinner a film is, the severer problems are in easiness of squash, protrusive deformation resistance and operation efficiency.

Plastic film condensers include two types of condensers, a metallized film condenser and a film-foil condenser, in both of which same requirements are imposed on the film. With respect to these condensers, various investigations have been made on workability during winding of a film and during forming of a wound element as disclosed, for example, in Japanese Patent Publication No. 42-24099.

The easiness of squash shows whether a wound element is easily crushed or not. The dielectric breakdown voltage of elements having a reduced easiness of squash will be low because higher pressures are required at pressing. In addition, the size of such elements will fall short of standard requirements because elements cannot be accurately pressed. A relatively large proportion of final products will be rejected as defective.

Another factor to be considered is the protrusive deformation resistance. The protrusive deformation means that when a film is wound into a roll the film is locally protruded due to the inclusion of foreign matters. Consequently, the film is deformed in a loop-like shape at locally protruded portions so that the dielectric breakdown voltage is lowered. This also causes a high rate of rejection of final products. Of course, a thinner film may be more susceptible to deformation.

The easiness of squash and protrusive deformation resistance of polyethylene terephthalate films may be improved by blending fine particles therein. However, blended fine particles may lower the dielectric breakdown voltage which is also a requirement. Therefore, the most important point to be considered when particles are added to films for use in condensers resides in the selection of the particles which do not reduce the dielectric breakdown voltage and increase the easiness of squash and protrusive deformation resistance, because the dielectric breakdown voltage depends largely on the kind of particles, provided that particle sizes are equal. Furthermore, the life of a filter placed in an extruder plays an important role when a condenser film is formed. If foreign matter, other than the particles to be added, or a coagulated mass of the particles is present in the condenser film, the dielectricc breakdown voltage is lowered and failure may often occur at the time of film formation. To avoid such inconveniences, a filter of maximum fineness should be selected as the filter placed in an extruder. Therefore, particles which may readily coagulate are unsuitable as the additive for a condenser film composition.

The inventors have found that the easiness of squash of a condenser film cannot be increased only by improving its friction coefficient because other factors, including the irregularity of film surface have complicated the relationship and the type of particles has an influence. It has been also found that the kind, particle size, and additive amount of particles have close relation to the protrusive deformation resistance.

According to another important aspect of the invention, there is provided a polyethylene terephthalate film suitable for use in condensers which comprises polyethylene terephthalate containing 0.1 to 0.4% by weight of granular calcium terephthalate anhydride having a volume shape factor $\phi_v$ of 0.08 to 0.4 and an average particle diameter of 0.5 to 3 microns. The portion of the anhydride particles which consists of particles having a particle size of 1 to 2.5 microns should be 0.08% to 0.3% by weight and another portion consisting of larger particles having a particle size of 5 microns or more should be not more than 0.02% by weight.

In this second embodiment of the invention, the calcium terephthalate anhydride particles have a particle size between 0.5 and 3 microns and are added in an amount between 0.1 and 0.4% by weight. If the total amount of particles added does not reach 0.1% by weight, no additive effect improving the easiness of squash is observed. On the other hand, if the total amount exceeds 0.4% by weight, the protrusive deformation resistance, dielectric breakdown voltage, and filter life are reduced.

According to the invention, the particles should be added so that particles having a particle size of 1 to 2.5 microns are 0.08 to 0.3% by weight, preferably 0.08 to 0.25% by weight and particles having a particle size of 5 microns or more (and preferably, a maximum diameter of not more than 20 microns) are 0.02% by weight or less, preferably 0.015% by weight or less in the film.

In general, the protrusive deformation resistance of a film is better when particles added have a larger particle size. However, if particles having a particle size of more than 2.5 microns are present in a relatively larger proportion, the dielectric breakdown voltage and filter life are reduced and the film is often ruptured upon forming. Consequently, particles of more than 2.5 microns in particle size should be involved in a lesser proportion. On the other hand, if particles added have a particle size of not more than 1 micron, the protrusive deformation resistance is increased no more and the easiness of squash is improved only to a small extent. It is preferred that the particle size of a major portion of calcium terephthalate anhydride particles falls within the range between 1 and 2.5 microns. If the amount of particles of 1 to 2.5 microns in particle size is less than 0.08% by weight, no additive effect on the easiness of squash is observed and if the amount exceeds 0.3% by weight, the protrusive deformation resistance, dielectric breakdown voltage, and filter life are reduced.

As described above, larger particles having a particle size of more than 2.5 microns may preferably be present in a lesser proportion. Illustratively, particles having a particle size of more than 5 microns may be less 0.02% by weight or less, preferably 0.015% by weight or less. If such larger particles (5 microns) are 0.02% by weight or more, the dielectric breakdown voltage and filter life are reduced.

The polyethylene terephthalate, compounded with the specified amount of the particles can maintain the filter life longer. It can provide a film improved in dielectric breakdown voltage, easiness of squash, and protrusive deformation resistance by extrusion into a sheet and stretching the sheet by more than three times in both the longitudinal and the transverse directions to disperse the particles over the film surface.

The invention will be understood more clearly with reference to the following examples; however, these examples are intended to illustrate the invention and are not to be construed to limit the scope of the invention.

Methods of determining physical and electrical properties are as follows.

Particle size

A microscope was used. A molded article of a polyester polymer was sliced into the thinnest possible specimen, which was then inserted between cover glasses. The surface of this specimen was photographed to determine the maximum diameter of each particle. The term "particle size" used herein indicates this maximum diameter. The average particle diameter is calculated by determining the weight distribution in a group of equivalent spherical particles having a diameter equal to the above-described maximum diameter. That is, a diameter given at an integrated weight fraction of 50% is considered as the average particle diameter.

Film haze

Haze was determined by means of a hazeometer, NDH-2A (manufactured and sold by *Nippon Denshoku*) according to the method of ASTM D1003-59T.

Friction coefficient

The method defined by ASTM 1894-63 was modified so as to make it possible to test a tape-like sample which was 15 mm in width and 150 mm in length. The determination was carried out at a speed of 20 mm/min. at a temperature of 21° ± 1° C and a relative humidity of 65 ± 5%.

Abrasion resistance

A film under a constant load was reciprocated through rolls and the amount of debris generated within a certain period was weighed. The results was classified in A, B and C sequence, beginning with the best (smaller amount).

Volume shape factor $\phi_v$

Measured values of the diameter of particles on the plane of photographs were used to obtain an arithmetic mean.

Figure 1A:
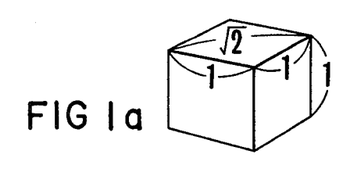
Figure 1B:
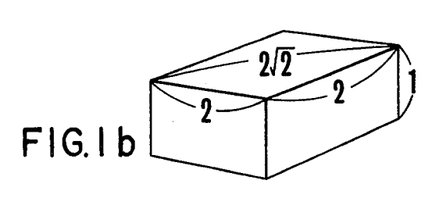
Figure 1C:
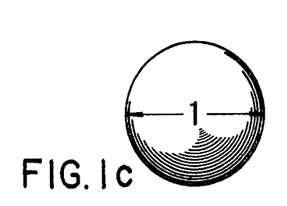

FIG. 1 shows three models of particles. FIG. 1-a shows a cubic model, FIG. 1-b a rectangular parallelopipedon and FIG. 1-c a sphere. For each case the valume shape factor $\phi_v$ is represented as follows:

$$\phi_v = 1/(\sqrt{2})^3 \div 0.35 \tag{a}$$

$$\phi_v = 4/(2\sqrt{2})^3 \div 0.18 \tag{b}$$

$$\phi_v = 4/3 \pi (\tfrac{1}{2})^3/1^3 = \pi/6 \div 0.52 \tag{c}$$

Scratch

On the aluminum surface of an aluminum-deposited (thickness 500 A) film was superposed another sample film and a predetermined load was applied on the top of the superposed film. In this loaded condition, the lower Al-deposited film was pulled to slide along under the upper film at a speed of 20 mm/min. Thereafter, the Al-deposited film was taken out and subjected to the determination of total transmissitivity T with a hazeometer, NDH-2A (manufactured and sold by Nippon Denshoku). The total transmissivity determined at a load of 30 g/cm² is $T_1$ and the total transmissivity at a load of 80 g/cm² is $T_2$. It is to be noted that both $T_1$ and $T_2$ will be O when no scratch is formed.

Difference between the right side and the reverse side

In a vacuum metallizer two samples were placed and deposited with aluminum at the same time. One of the samples was laid with the polyethylene terephthalate side above, while the other was laid with the aluminum side above. The difference was evaluated with the naked eye. Samples were rated A, B, C, or D in sequence from the best to the worst. The samples rated A or B are acceptable.

Protrusive deformation

In the course of winding up a film, large particles having an average particle diameter of 10 microns were introduced on purpose to locally protrude the surface of the subsequent overlapped portion of the film. Then the film was further wound until the local protrusion disappeared. The number of turns of the film was recorded. The results was classified A, B, or C, A indicating the best.

Easiness of squash

A load applied to a wound element was gradually increased. Value of the load at which the deformation commenced and terminated were recorded, respectively. The results were classified A, B, or C, as above.

Dielectric breakdown voltage

A 100-KV dielectric breakdown testing machine (OEL-72034, manufactured by Toyo Seki) was used. The applied voltage was gradually increased and the voltage at which a test film under test broke down and showed a short was recorded. The results were classified in A, B, or C, A indicating with the best.

Filter life

A 1500-mesh filter having a filtration area of 31.2 cm² was placed in an extruder and a molten polymer was extruded at a rate of 8.5 kg/hr. The output of the extruder was recorded until the pressure at the entrance of the filter reached 250 kg/cm². The results were again classified A, B, or C.

A film having a value for protrusive deformation resistance, easiness of squash, dielectric breakdown voltage, or filter life of C was rejected because such a film cannot be used in practice.

In the following examples and comparative examples, parts are by weight. The concentration of a polyester-insoluble compound formed in the polyesters of Examples 7 – 10 and 13 and Comparative Example 1 is written in parentheses in the column of added amount in Table 1 as a film haze (%) measured when the polyester is formed into a film of 12 microns in thickness. When two kinds of polyesters are blended, the additive amount, solution haze and haze are expressed in terms of measured or calculated values for the resulting polyester.

EXAMPLE 1

Preparation of calcium terephthalate

In a 20-1 container equipped with an agitator was placed 3.0l of an aqueous solution of 10 wt/vol % of calcium chloride. With stirring 11.3 l of another aqueous solution of 5 wt/vol % of sodium terephthalate was added thereto. Upon addition, the solution instantaneously became milky turbid, which indicated the formation of calcium terephthalate. The agitation was continued for 30 minutes. Next, solids liquid separateion was carried out to obtain calcium terephthalate trihydride, which was then dried at 40° C under reduced pressure for 2 hours. The resulting particles were plate particles with a thickness of 2 to 4 microns and a maximum diameter of 10 to 30 microns.

Figure 2:
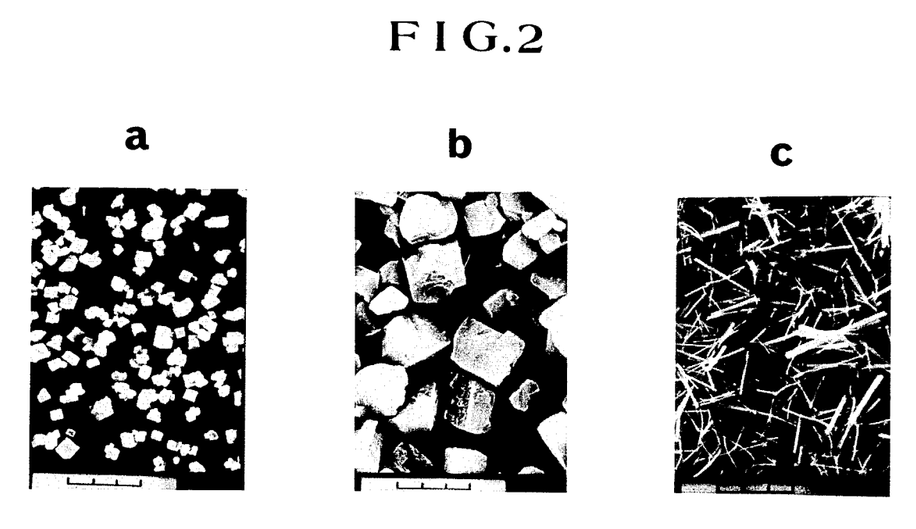

Next, a portion sampled from the calcium terephthalate particles was heated at 200° C for 2 hours to form its anhydride and then cooled. The anhydride particles were ground at a rate of 800 g/min. and under an air pressure of 6.0 kg/cm² in a jet mill grinding machine (Aeroplex 200 AS, manufactured by Alpine Co.) to a particle size in the order of 2 to 6 microns. Then the classification of particles was carried out by means of an air classifier (Alpine Multiplex 100 MZR) according to the following conditions. Sample supply rate: 45 g/min.; restriction of the lower limit, revolution of the classifier: 9,000 rpm, flow rate of air: 46 m³/hr.; restriction of the upper limit, revolution of the classifier: 7,000 rpm, flow rate of air: 48 m²/hr. There were obtained granular calcium terephthalate anhydride particles having an average particle diameter of 4.0 microns and $\phi_\nu$ = 0.25. The obtained particles were photographed, and are shown in FIGS. 2-a and 2-b. The calcium terephthalate anhydride particles were dispersed in ethylene glycol to form a 10 wt/vol% slurry.

Production of a film

In an ester-interchange tank were placed 100 parts of dimethyl terephthalate, 75 parts of ethylene glycol and 0.03 part of manganese acetate. The contents were gradually heated to facilitate the ester-interchange reaction and distill off the methanol formed and excess ethylene glycol.

To the reaction mixture was added 0.4 part of the above prepared slurry of calcium terephthalate in ethylene glycol. (The amount of calcium terephthalate added corresponds to 0.04% by weight of the polyester. The amount of particles added represented in terms of % by weight are all based on the polyester, hereinafter.) Further, 0.03 part of antimony trioxide and 0.03 part of phosphorous acid were added. Condensation polymerization was carried out under a reduced pressure of 0.5 mmHg for 4 hours. There was obtained a polyester compound containing calcium terephthalate particles which was then melted at 290° C and extruded through a T-type die into a film of 150 microns in thickness. The film was stretched at 80° – 90° C by 3.5 times in the longitudinal direction and then by 3.5 times in the crosswise direction.

The film having a thickness of 12 microns thus obtained was subjected to measurements of slipperiness, haze and abrasion resistance. The results are shown in Table 1.

EXAMPLE 2

Example 1 was repeated except that the amount of the calcium terephthalate anhydride particles added was 0.07% by weight.

EXAMPLE 3

Example 1 was repeated except that the amount of the calcium terephthalate anhydride particles added was 0.15% by weight.

EXAMPLE 4

Example 1 was repeated except that 0.07% by weight of calcium terephthalate anhydride particles prepared in similar manner as described in Example 1 and having $\phi_v = 0.14$ was added.

EXAMPLE 5

Example 4 was repeated except that the amount of the calcium terephthalate anhydride particles added was 0.15% by weight.

EXAMPLE 6

Example 1 was repeated except that 0.07% by weight of calcium terephthalate anhydride particles prepared in similar manner as described in Example 1 and having an average particle diameter of 4.5 microns and $\phi_v = 0.18$ was added.

COMPARATIVE EXAMPLE 1

In a reactor were placed 100 parts of dimethyl terephthalate, 75 parts of ethylene glycol and 0.08 part of calcium acetate. The contents were gradually heated to facilitate the reaction and distill off the methanol formed and excess ethylene glycol. Next, 0.03 part of antimony trioxide was added. The temperature was gradually raised from 230° C to 280° C, while the pressure was slowly reduced from atmospheric pressure to 0.5 mmHg. There was obtained a polyester compound which contained particles consisting of calcium terephthalate and a polyester oligomer calcium salt and having a particle size of about 5 microns.

The polyester compound was processed in a similar manner as described in Example 1 into a film having a thickness of 12 microns.

EXAMPLE 7

Comparative Example 1 was repeated to obtain a polyester which results in a film having a film haze of 1.3%. This polyester was blended with the polyester obtained in Example 1 in equal amounts. A film was formed from the blend.

EXAMPLE 8

Comparative Example 1 was repeated except that 0.06 part of calcium acetate was added. There was obtained a polyester which resulted in a film having a film haze of 2.0%. Separately, a polyester which included 0.10% by weight of calcium terephthalate anhydride particles prepared in an identical manner as described in Example 1 and having an average particle diameter of 4.0 microns and $\phi_v = 0.25$ was produced. Both the polyesters were blended in equal amounts. A film was formed from the blend.

EXAMPLE 9

In a reactor were placed 100 parts of dimethyl terephthalate, 75 parts of ethylene glycol and 0.05 part of calcium acetate. The contents were gradually heated to facilitate the reaction and distill off the methanol formed and excess ethylene glycol. Next, 0.03 part of antimony trioxide and 0.05 part of terephthalic acid were added. The temperature was gradually raised from 230° to 280° C, while the pressure was slowly reduced from atmospheric pressure to 0.5mmHg. There was obtained a polyester compound which resulted in a film having a film haze of 2.4%. The calcium terephthalate particles precipitated in the polyester compound had a particle size of about 2 microns.

Separately, a polyester which included 0.10% by weight of calcium terephthalate anhydride particles used in Example 4 and having an average particle diameter of 4.0 microns and $\phi_v = 0.14$ was produced. Both the polyesters were blended in equal amounts. A film was formed from the blend.

EXAMPLE 10

In a reactor were placed 100 parts of dimethyl terephthalate, 75 parts of ethylene glycol and 0.08 part of calcium acetate. The contents were gradually heated to facilitate the reaction and distill off the methanol formed and excess ethylene glycol. Next, 0.07 part of antimony trioxide and 0.06 part of phosphoric acid were added. Polymerization was carried out in the conventional manner to obtain a polyester. The particles precipitated in the polyester had a particle size of about 3 microns.

A portion sampled from the polyester compound was dissolved in orthochlorophenol and then subjected to centrifugal separtion to separate the particles. Spectral analysis of the particles showed that more than 1% by weight of calcium, antimony and phosphorus are contained in each particle, respectively.

The polyester compound was blended with the polyester compound obtained in Example 6 in equal amounts. A film was formed from the blend according to the procedure described in Example 1.

COMPARATIVE EXAMPLE 2

According to the preparation of calcium terephthalate described in Example 1, plate particles of calcium terephthalate trihydride having a thickness of 2 - 4 microns and a maximum diameter of 10 - 30 microns were prepared. The particles were dried at 40° C under reduced pressure for 2 hours to remove adhering water.

Analysis of the resulting compound showed C : 37.0%, H : 4.0%, Ca : 15.5%. These values correspond to the calculated values for calcium terephthalate trihydride, The calcium terephthalate trihydride particles were ground and classified in similar manner as described in Example 1, obtaining granular particles having an average particle diameter of 4.0 microns and $\phi_v = 0.25$. The granular calcium terephthalate trihydride particles were dispersed in ethylene glycol to form a 10 wt/vol % slurry, which was stored.

Production of a polyester was carried out in a similar manner as described in Example 1 except that the above slurry was used instead of the granular calcium terephthalate anhydride/ethylene glycol slurry. There was obtained a polyester compound including 0.04% by The results from Examples 2 – 13 and Comparative Examples 1 – 2 are shown in Table 1.

Table 1

|  | Particle | | | | Film | | |
| --- | --- | --- | --- | --- | --- | --- | --- |
|  | Kind* | Average particle (μ) diameter | $\phi_v$ | Added amount (wt %) (haze, %) | Slipperiness | Haze (%) | Abrasion resistance |
| Example 1 | CTA | 4.0 | 0.25 | 0.04 | 0.58 | 1.7 | A |
| Example 2 | CTA | 4.0 | 0.25 | 0.07 | 0.52 | 3.0 | A |
| Example 3 | CTA | 4.0 | 0.25 | 0.15 | 0.45 | 5.9 | A |
| Example 4 | CTA | 4.0 | 0.14 | 0.07 | 0.51 | 3.0 | A |
| Example 5 | CTA | 4.0 | 0.14 | 0.15 | 0.46 | 6.0 | A |
| Example 6 | CTA | 4.5 | 0.18 | 0.07 | 0.52 | 2.9 | A |
| Example 7 | CTA | 4.0 | 0.25 | 0.02 | 0.59 | 1.5 | A |
|  | Precipd. Ca | about 6 | — | (0.65) | | | |
| Example 8 | CTA | 4.0 | 0.25 | 0.05 | 0.52 | 3.0 | A |
|  | Precipd. Ca | about 5 | — | (1.0) | | | |
| Example 9 | CTA | 4.0 | 0.14 | 0.05 | 0.53 | 3.2 | A |
|  | Precipd. Ca | about 2 | — | (1.2) | | | |
| Example 10 | CTA | 4.5 | 0.18 | 0.035 | 0.55 | 2.3 | A |
|  | Precipd. Ca | about 3 | — | (0.85) | | | |
| Example 11 | CTA | 4.0 | 0.25 | 0.04 | 0.59 | 1.7 | A |
| Example 12 | CTA | 3.5 | 0.20 | 0.04 | 0.60 | 1.6 | A |
| Example 13 | CTA | 3.5 | 0.20 | 0.04 | 0.54 | 3.0 | A |
|  | Precipd. Ca | about 5 | — | (1.3) | | | |
| Comparative Example 1 | Precipd. Ca | about 5 | — | (2.9) | 0.60 | 2.9 | C |
| Comparative Example 2 | CAW | 4.0 | 0.25 | 0.04 | 0.72 | 1.8 | R~C |

*CTA: Calcium terephthalate anhydride
CTW: Calcium terephthalate having water of crystallization
Precipd. Ca: Precipitated calcium compound weight of calcium terephthalate. It was found that the particles included in the polyester were needle particles having a length of about 15 microns and a diameter of 1 – 2 microns, in other words, the particles had changed their shape from the initial granular shape before the dispersion in ethylene glycol to a different shape. A film having a thickness of 12 microns were formed from the obtained polyester compound.

EXAMPLE 11

In a reactor were placed 100 parts of dimethyl terephthalate, 75 parts of ethylene glycol and 0.08 part of calcium acetate. The contents were gradually heated to facilitate the reaction and distill off the methanol formed and excess ethylene glycol. After the ester-interchange reaction, 0.035 part of phosphoric acid and 0.04 part of calcium terephthalate anhydride particles prepared in an identical manner as described in Example 1 and having an average particle diameter of 4.0 microns and $\phi_v = 0.25$ were added to the reaction mixture. Further, 0.03 part of antimony trioxide was added. Condensation polymerization was carried out to produce a polyester. Finally, a film having a thickness of 12 microns was formed.

EXAMPLE 12

Example 11 was repeated except that calcium terephthalate anhydride prepared in a similar manner as described in Example 1 and having an average particle diameter of 3.5 microns and $\phi_v = 0.20$ was added. A film was formed.

EXAMPLE 13

Example 12 was repeated except that 0.02 part of phosphoric acid was added. A film was formed.

EXAMPLE 14

Preparation of calcium terephthalate

According to the preparation of calcium terephthalate described in Example 1, plate particles of calcium terephthalate anhydride having a thickness of 2 – 4 microns and a maximum diameter of 10 – 30 microns were prepared.

Next, a portion sampled from the calcium terephthalate particles was ground for 1 hour in a ball mill and then dispersed in ethylene glycol to form a 10 wt/vol % slurry. A part of the slurry was subjected to centrifugal classification to separate granular calcium terephthalate anhydride particles which had an average particle diameter of 0.2 microns and $\phi_v = 0.15$.

Production of a film

In an ester-interchange reaction tank were placed 100 parts of dimethyl terephthalate, 75 parts of ethylene glycol and 0.03 part of manganese acetate. The contents were gradually heated to facilitate the ester-interchange reaction and distill off the methanol formed and excess ethylene glycol. To the reaction mixture were added 0.03 part of antimony trioxide and the above-prepared ethylene glycol slurry of calcium terephthalate anhydride having an average particle diameter of 0.2 microns. The amount of calcium terephthalate anhydride was 0.20% by weight of the polyester. Further, 0.03 part of phosphorous acid was added. Condensation polymerization was carried out for 4 hours at 280° C and under a reduced pressure of 0.5 mmHg. The obtained polyester compound was molten at 290° C and extruded through a die into a sheet, which was in turn stretched at a temperature above the glass tansition temperature by 3.5 times in both the longitudinal and the crosswise directions, obtaining a film of 12 microns in thickness. The friction coefficient, film haze, difference between the right side and the reverse side and scratch influence on the surface of a deposited aluminum were determined for the film.

The results are shown in Table 2.

EXAMPLES 15–22

Example 14 was repeated except that calcium terephthalate anhydride particles prepared in a similar manner as described in Example 14 and having an average particle diameter of 0.2, 0.5, 1.0, 2.0 and 3.0 microns are added in different amounts in respective Examples.

The results are shown in Table 2.

cle diameter of 1.0 micron. Properties necessary as the condenser film were determined for the films. The results are shown in Table 3.

EXAMPLES 24–31

To a polyester oligomer prepared in an identical manner as described in Example 14 were added different amounts of calcium terephthalate anhydride prepared in a similar manner as described in Example 23 and having different particle sizes. Condensation polymerization was carried out under similar conditions as described in Example 1. The resulting polymer compounds were formed into films under similar conditions as described in Example 23, respectively, which films Table 2

| | Addition Condition | | | | Friction coefficient | | Film haze thickness 12 μ (%) | Total transmissivity | | Difference between the right side and the reverse side |
|---|---|---|---|---|---|---|---|---|---|---|
| | Average particle diameter X (μ) | $\phi_\nu$ | Added amount Y (wt %) | X.Y | static | dynamic | | $T_1$ (%) | $T_2$ (%) | |
| Example 14 | 0.2 | 0.15 | 0.20 | 0.04 | 0.70 | 0.60 | 2.2 | 1.8 | 1.8 | A |
| Example 15 | 0.2 | 0.15 | 0.30 | 0.06 | 0.45 | 0.44 | 2.9 | 1.9 | 2.0 | B |
| Example 16 | 0.5 | 0.20 | 0.10 | 0.05 | 1.50 | 0.85 | 1.4 | 1.7 | 1.9 | A |
| Example 17 | 0.5 | 0.20 | 0.30 | 0.15 | 0.45 | 0.40 | 4.0 | 2.0 | 2.3 | B |
| Example 18 | 1.0 | 0.18 | 0.05 | 0.05 | 2.35 | 1.85 | 1.2 | 1.6 | 1.7 | A |
| Example 19 | 1.0 | 0.18 | 0.10 | 0.10 | 0.76 | 0.49 | 2.4 | 1.8 | 1.9 | B |
| Example 20 | 2.0 | 0.20 | 0.05 | 0.10 | 1.85 | 0.85 | 1.9 | 2.0 | 2.4 | B |
| Example 21 | 3.0 | 0.20 | 0.02 | 0.06 | 2.33 | 1.64 | 0.8 | 1.6 | 1.7 | B |
| Example 22 | 3.0 | 0.20 | 0.05 | 0.15 | 1.75 | 0.83 | 1.9 | 2.0 | 2.4 | B |

EXAMPLE 23

According to the procedures as described in Example 14, calcium terephthalate anhydride particles having a thickness of 2–4 microns and a maximum diameter of 10 – 30 microns were prepared.

Next, a portion sampled from the calcium terephthalate anhydride particles was ground for 1 hour in a ball mill and then dispersed in ethylene glycol to form a 10 wt/vol % slurry. A part of the slurry was subjected to centrifugal classification to separate granular calcium terephthalate anhydride particles which had an average particle diameter of 1.0 micron and $\phi_\nu = 0.18$.

According to the film production process as described in Example 14, two kinds of films having a thickness of 6 and 8 microns, respectively, were formed, each film containing 0.25% by weight of calcium terephthalate anhydride particles having an average partiwere subjected to measurements on various properties.

COMPARATIVE EXAMPLES 3 – 7

To a polyester oligomer prepared in an identical manner as described in Example 14 were added different amounts of fine particles of LiF, SiC and CaCO₃ which had been dispersed and classified. Polymerization was carried out under similar conditions as described in Example 1. The resulting polymer compounds were formed into films under similar conditions as described in Example 23, respectively, which films were subjected to measurements on various properties.

The results from Examples 24 – 31 and Comparative Examples 3 – 7 are shown in Table 3.

Table 3

| | Particle | | | | | | Film | | | | |
|---|---|---|---|---|---|---|---|---|---|---|---|
| | Kind* | Average particle diameter (μ) | $\phi_\nu$ | Added amount (wt %) | Amount of 1-2.5 μ particles (wt %) | Amount of >5μ particles (wt %) | Friction coefficient | | Dielectric breakdown voltage | Protrusive deformation resistance | Easiness of squash | Filter life |
| | | | | | | | static | dynamic | | | | |
| Example 23 | CTA | 1.0 | 0.18 | 0.25 | 0.12 | 0 | 0.55 | 0.41 | A | B | B | A |
| Example 24 | CTA | 1.5 | 0.20 | 0.20 | 0.14 | 0 | 0.54 | 0.40 | A | A B | A B | A |
| Example 25 | CTA | 2.0 | 0.20 | 0.20 | 0.12 | 0 | 0.52 | 0.39 | A | A | A | A |
| Example 26 | CTA | 2.5 | 0.25 | 0.20 | 0.10 | 0.006 | 0.57 | 0.38 | A | A | A | A |
| Example 27 | CTA | 2.5 | 0.25 | 0.20 | 0.09 | 0.016 | 0.56 | 0.38 | B | A | A | B |
| Example 28 | CTA | 2.0 | 0.20 | 0.15 | 0.09 | 0 | 0.63 | 0.38 | A | B | B | A |
| Example 29 | CTA | 2.3 | 0.20 | 0.20 | 0.10 | 0.014 | 0.54 | 0.38 | A | B | B | A |
| Example 30 | CTA | 2.0 | 0.20 | 0.25 | 0.15 | 0 | 0.53 | 0.38 | A | A | A | A |
| Example 31 | CTA | 1.5 | 0.20 | 0.35 | 0.25 | 0 | 0.50 | 0.37 | B | A | A | B |
| Comparative Example 3 | LiF | 2.5 | | 0.25 | 0.14 | 0.013 | 0.54 | 0.41 | C | A | A | A |
| Comparative Example 4 | SiC | 2.5 | | 0.25 | 0.13 | 0.013 | 0.53 | 0.39 | C | A | A | A |
| Comparative Example 5 | CaCO₃ | 1.0 | | 0.25 | 0.14 | 0 | 0.56 | 0.42 | A | B | B | C |
| Comparative Example 6 | CaCO₃ | 2.0 | | 0.25 | 0.15 | 0 | 0.53 | 0.38 | A | A | A | C |
| Comparative Example 7 | CaCO₃ | 3.0 | | 0.25 | 0.08 | 0.013 | 0.55 | 0.40 | A | A | A | C |

*CTA : Calcium terephthalate anhydride

As seen from data in Tables 1 – 3, the polyester films of the invention in Examples are all satisfactory, while the films in comparative Examples are not satisfactory.

This means that calcium terephthalate having water of crystallization gives films with low abrasion resistance and poor relation of slipperiness to haze. Properties appropriate as a film are substantially reduced in the presence of water of crystallization.

A polyester film which includes 0.02 to 0.3% by weight of calcium terephthalate anhydride particles having an average particle diameter of 0.2 to 3.0 microns according to the first preferred embodiment of the invention is particularly suitable as a deposition-receptive film.

Another polyester film which includes 0.1 to 0.4% by weight of calcium terephthalate anhydride particles having an average particle diameter of 0.5 to 3.0 microns, particles of 1.0 to 2.5 microns in particle size being 0.08 to 0.3% by weight and larger particles of more than 5 microns in particle size being less than 0.02% by weight, according to the second preferred embodiment of the invention, is particularly suitable as a condenser film. As obvious from data of Comparative Examples 3 – 7, the dielectric breakdown voltage is too low in case of LiF and SiC and the filter life is too short in case of $CaCO_3$ because of outstanding coagulation.

EXAMPLE 32

In a ester-interchange reaction tank were placed 100 parts of dimethyl terephthalate, 75 parts of ethylene glycol and 0.08 part of calcium acetate. The contents were gradually heated to facilitate the ester-interchange reaction and to distill off the methanol formed and excess ethylene glycol. To the reaction mixture were added 0.03 part of antimony trioxide and a fixed amount of under-mentioned calcium terephthalate A, B and C to carry out polycondensation reaction at 280° C for 4 hours and under a reduced pressure of 0.5 mmHg.

The calcium terephthalate used herein was prepared by the following procedures:

Calcium terephthalate A: In a container, inner volume of 1l, having an stirrer were placed 300 ml of calcium chloride aqueous solution of 2 wt/vol% and then added 567 ml of potassium terephthalate aqueous solution of 2 wt/vol% was added with stirring. Upon the addition, the solution became cloudy due to formation of calcium terephthalate. The precipitate was filtered after 30 minutes stirring and then dried at 60° C for 2 hours to remove adhering water. As the result of elementary analysis, the values of the compound A correspond to the calculated values of calcium terephthalate trihydride, and an average particle size of the compound A being 5 microns × 5 microns × 2 microns and $\phi_v = 0.14$.

Calcium terephthalate B: The compound B was obtained by heating the compound A at 200° C for 2 hours. The analytical values of the compound B correspond substantially to calculated values of anhydride thereof.

Calcium terephthalate C: The compound C was obtained by heating the compound A at 140° C for 30 minutes. The compound C was essentially compound A with the water of crystallization partially removed.

Table 4

| Elemental analysis | Analytical value | | | Calculated value | | |
|---|---|---|---|---|---|---|
| | C(%) | H(%) | Ca(%) | C(%) | H(%) | Ca(%) |
| compound A (trihydride salt) | 36.9 | 4.0 | 15.4 | 37.2 | 3.9 | 15.5 |
| compound B (anhydride) | 46.8 | 2.1 | 19.2 | 47.0 | 2.0 | 19.6 |
| compound C | 40.1 | 3.3 | 16.6 | | | |

Properties of the thus obtained polyethylene terephthalate films are shown in Table 5.

Table 5

| Test No. | Added kind | Calcium terephthalate weight % to polymer | Formed polymer | | |
|---|---|---|---|---|---|
| | | | maximum viscosity | melting point | color |
| 1 | B | 1.0 | 0.651 | 262° C | white |
| 2 | B | 3.0 | 0.650 | 262 | white |
| 3 | A | 1.0 | 0.645 | 262 | faint yellow |
| 4 | A | 3.0 | 0.651 | 261 | light red |
| 5 | C | 1.0 | 0.648 | 262 | soft yellow |
| 6 | C | 3.0 | 0.651 | 262 | faint yellow |

Test Nos. 1 and 2 in the Table were carried out in accordance with the present invention, where the polyester had sufficient whiteness. Test Nos. 3 – 6 (Comparative Examples) were the cases where calcium terephthalate from which water of crystallization was insufficiently removed due to inadequate heating, and the polymer exhibited yellowish or reddish color.

Next, a film was prepared by using polymer (1) obtained by Test No. 1 in the following manner: Polyester (2) prepared from 100 parts of dimethyl terephthalate and 75 parts of ethylene glycol as the starting materials, 0.03 part of manganese acetate as ester-interchange catalyst, 0.01 part of germanium dioxide and 0.04 part of phosphorous acid and the above-mentioned polymer (1) were uniformly blended in a weight ratio of 3 : 1 (the concentration of calcium terephthalate was 0.25% by weight of the polymer). The mixture was then melted at 290° C and extruded through a T-die to form a film of 150 microns in thickness. The film was stretched by 3.5 times in the longitudinal direction at 80° – 90° C and then by 3.5 times in the traverse direction which was followed by heat fixation at 220° C. The thus obtained films, being 12 microns thick were rolled up. The section of the rolled film was observed as white color, and there was no recognition of unfavourable color.

Polymer (3) obtained by Test No. 3 and polymer (2) given above were blended in a weight ratio of 3 : 1 and to produce a rolled film of 12 microns in thickness in accordance with the manner above. However, a light yellow color was observed at the edge of the rolled film which is considered commercially unacceptable.

What is claimed is:

1. A polyester film comprising a polyester mainly consisting of polyethylene terephthalate and 0.02 to 0.4% by weight of calcium terephthalate anhydride particles incorporated into the polyester by addition to the reaction medium in which the polyester is formed, said calcium terephthalate anhydride particles having an average particle diameter of 0.2 to 4.5 microns and a volume shape factor, $\phi v$, in the range of 0.08 to 0.4, said $\phi v$ being calculated by the formula:

$$\phi v = V/D^3$$

wherein D is the maximum diameter of a particle in the projection plane and V is the volume of the particle, said particulate calcium terephthalate anhydride being formed by reacting a dialkali metal terephthalate with a water-soluble calcium compound and heating the resultant calcium terephthalate to a temperature above 100° C to convert it into its anhydride.

2. The film of claim 1 wherein the particulate calcium terephthalate anhydride has the approximate empirical formula:

* * * * *

UNITED STATES PATENT AND TRADEMARK OFFICE
CERTIFICATE OF CORRECTION

PATENT NO. : 4,101,523
DATED : July 18, 1978
INVENTOR(S) : Masamichi WATANABE, et al It is certified that error appears in the above-identified patent and that said Letters Patent are hereby corrected as shown below:

Column 5, line 40, before "lower" insert --and--; and delete "is".

Column 8, below line 57
change "$\phi\nu =1/(\sqrt{2})^3 \div 0.35$" to --$\phi\nu =1/(\sqrt{2})^3=0.35$--.

change "$\phi\nu =4/(2\sqrt{2})^3 \div 0.18$" to --$\phi\nu=4/(2\sqrt{2})^3 =0.18$-- change "$\phi\nu 4/3\pi (\frac{1}{2})^3 /1^3 = \pi/6 \div 0.52$" to
-- $\phi\nu= 4/3\pi (\frac{1}{2})^3 /1 = \pi/6 = 0.52$--.

Column 9, line 41, change "Toyo Seki" to -- Toyo Seiki--;

Table 1, the last entry under the second column having the heading "Kind*", "CAW" to --CTW--.

Column 18, lines 1 and 2, "telephthalate films" is to --terephthalate--.

Signed and Sealed this

Ninth Day of October 1979

[SEAL]

Attest:

RUTH C. MASON
Attesting Officer

LUTRELLE F. PARKER
Acting Commissioner of Patents and Trademarks